US009799433B2

(12) United States Patent
Eguchi et al.

(10) Patent No.: US 9,799,433 B2
(45) Date of Patent: Oct. 24, 2017

(54) SUPERCONDUCTING MAGNET

(71) Applicant: MITSUBISHI ELECTRIC CORPORATION, Chiyoda-ku, Tokyo (JP)

(72) Inventors: Ryo Eguchi, Tokyo (JP); Shoichi Yokoyama, Tokyo (JP); Hajime Tamura, Tokyo (JP); Tatsuya Inoue, Tokyo (JP)

(73) Assignee: MITSUBISHI ELECTRIC CORPORATION, Chiyoda-Ku, Tokyo (JP)

( * ) Notice: Subject to any disclaimer, the term of this patent is extended or adjusted under 35 U.S.C. 154(b) by 62 days.

(21) Appl. No.: 14/903,459

(22) PCT Filed: Jul. 11, 2013

(86) PCT No.: PCT/JP2013/068948
§ 371 (c)(1),
(2) Date: Jan. 7, 2016

(87) PCT Pub. No.: WO2015/004766
PCT Pub. Date: Jan. 15, 2015

(65) Prior Publication Data
US 2016/0233011 A1    Aug. 11, 2016

(51) Int. Cl.
*H01F 6/04*     (2006.01)
*A61B 5/055*    (2006.01)
(Continued)

(52) U.S. Cl.
CPC ............... *H01F 6/04* (2013.01); *A61B 5/055* (2013.01); *G01R 33/3804* (2013.01);
(Continued)

(58) Field of Classification Search
CPC ... G01R 33/3804; G01R 33/3815; H01F 6/06; H01F 6/008; H01F 6/04; H01F 6/00; H01F 6/02
See application file for complete search history.

(56) References Cited

U.S. PATENT DOCUMENTS 5,650,903 A * 7/1997 Gross .................. H01F 6/02
361/141
5,999,383 A * 12/1999 Hall .................... H01F 6/02
174/125.1
(Continued)

FOREIGN PATENT DOCUMENTS

CN    101894652 A    11/2010
CN    101900794 A    12/2010
(Continued)

OTHER PUBLICATIONS

International Search Report (PCT/ISA/210) dated Sep. 17, 2013, by the Japanese Patent Office as the International Searching Authority for International Application No. PCT/JP2013/068948.
(Continued)

*Primary Examiner* — Bernard Rojas
(74) *Attorney, Agent, or Firm* — Buchanan Ingersoll & Rooney PC

(57) ABSTRACT

A superconducting magnet includes a superconducting coil, a refrigerant container, a radiation shield, a vacuum container, a refrigerating machine cooling an interior of the refrigerant container, a tubular current lead passing from outside of the vacuum container to inside of the refrigerant container electrically connected to the superconducting coil, a power source electrically connected to the current lead, a manometer measuring a pressure inside of the refrigerant container, a thermometer to measure a temperature of the current lead, and a control unit connected to each of the power source, the manometer, and the thermometer. The
(Continued)

control unit raises an output of the power source to vary a value of a current flowing into superconducting coil only when a measurement value of the manometer is higher than or equal to a set value and a measurement value of the thermometer is lower than or equal to a set value.

4 Claims, 6 Drawing Sheets

(51) Int. Cl.
    *H01F 6/00*           (2006.01)
    *G01R 33/3815*    (2006.01)
    *G01R 33/38*       (2006.01)
    *H01F 6/02*           (2006.01)
    *H01F 6/06*           (2006.01)

(52) U.S. Cl.
    CPC ........... *G01R 33/3815* (2013.01); *H01F 6/00* (2013.01); *H01F 6/008* (2013.01); *H01F 6/02* (2013.01); *H01F 6/06* (2013.01)

(56) References Cited

U.S. PATENT DOCUMENTS

| | | |
|---|---|---|
| 2010/0295640 A1 | 11/2010 | Tamura |
| 2010/0301977 A1 | 12/2010 | Tanabe |
| 2013/0123109 A1 | 5/2013 | Harrison |

FOREIGN PATENT DOCUMENTS

| | | |
|---|---|---|
| CN | 103106995 A | 5/2013 |
| JP | 60-54409 A | 3/1985 |
| JP | 62-224006 A | 10/1987 |
| JP | 63-133507 A | 6/1988 |
| JP | 02-306 A | 1/1990 |
| JP | 02-17808 U | 2/1990 |
| JP | 05-13826 A | 1/1993 |
| JP | 06-52160 U | 7/1994 |
| JP | 10-112407 A | 4/1998 |
| JP | 2001-110626 A | 4/2001 |
| JP | 2005-252085 A | 9/2005 |
| JP | 2009-278094 A | 11/2009 |
| JP | 2011-005091 A | 1/2011 |

OTHER PUBLICATIONS

Office Action (Decision to Grant Patent) dated Feb. 12, 2014, by the Japanese Patent Office in corresponding Japanese Patent Application No. 2013-557302, and an English Translation of the Office Action.
Ishibashi et al., "Development of disk fin type compact current leads", Cryogenic engineering, 1985, vol. 20, No. 3, pp. 159 to 165.
Kenji Ishibashi, "Current leads for superconducting magnets", Cryogenic engineering, 1989, vol. 24, No. 6, pp. 311 to 317.
Office Action dated Dec. 20, 2016, by the Chinese Patent Office in corresponding Chinese Patent Application No. 201380078149.5. (6 pages).

\* cited by examiner

SUPERCONDUCTING MAGNET

TECHNICAL FIELD

The present invention relates to a superconducting magnet, and particularly to a superconducting magnet having a current lead of a fixed type.

BACKGROUND ART

As a conventional art document disclosing a configuration of a magnetic system including a superconducting magnet having a current lead of a fixed type, Japanese Patent Laying-Open No. 2-000306 (PTD 1) is provided. In the superconducting magnet of the magnetic system disclosed in PTD 1, the current lead has a high thermal conductivity resistance. This reduces a quantity of heat introduced through the current lead when a magnetic coil is in a continuation mode (a mode in which a current does not flow through the current lead). Moreover, when a current flows through the current lead, helium gas flows from a refrigerant container through the current lead, so that the current lead is cooled automatically.

CITATION LIST

Patent Document

PTD 1: Japanese Patent Laying-Open No. 2-000306

SUMMARY OF INVENTION

Technical Problem

In the superconducting magnet disclosed in PTD 1, a flow rate of helium gas flowing through the current lead is adjusted by controlling opening and closing of a solenoid valve by means of a solenoid coil. When enough helium gas is not present in the refrigerant container, enough quantity of helium gas cannot flow through the current lead even if the solenoid valve is opened, thus the current lead cannot be cooled. When the current lead cannot be cooled, there is a possibility that the current lead is burned out by Joule's heat.

The present invention was made in view of the problem described above, and its object is to provide a superconducting magnet capable of preventing burn-out of a current lead.

Solution to Problem

A superconducting magnet in accordance with the present invention comprises a superconducting coil, a refrigerant container accommodating the superconducting coil which is in a state of being immersed in a liquid refrigerant, a radiation shield surrounding the refrigerant container, a vacuum container accommodating the superconducting coil, the refrigerant container, and the radiation shield, a refrigerating machine cooling an interior of the refrigerant container and the radiation shield, a tubular current lead passing from outside of the vacuum container to inside of the refrigerant container to constitute a flow path of said gasified refrigerant and electrically connected to the superconducting coil, a power source arranged outside of the vacuum container and electrically connected to the current lead, a manometer measuring a pressure inside of the refrigerant container, a thermometer arranged in the vacuum container to measure a temperature of the current lead, and a control unit connected to each of the power source, the manometer, and the thermometer. The control unit raises an output of the power source to vary a value of a current flowing into the superconducting coil only when a measurement value of the manometer is higher than or equal to a set value and a measurement value of the thermometer is lower than or equal to a set value.

Advantageous Effects of Invention

According to the present invention, burn-out of the current lead can be prevented.

DESCRIPTION OF EMBODIMENTS

Figure 1:
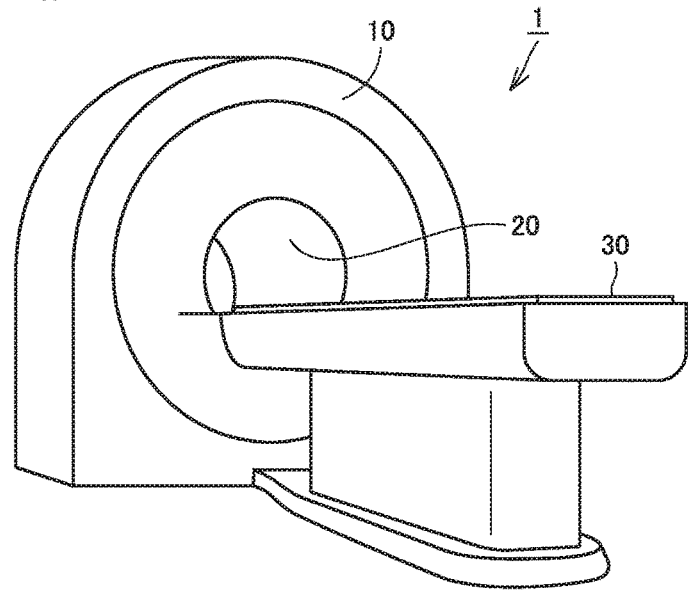
FIG. 1 is a perspective view representing an appearance of an MRI apparatus.

Hereinafter, a superconducting magnet in accordance with a first embodiment of the present invention will be described with reference to the drawings. In the following description of the embodiment, the same or corresponding portions in the drawings have the same reference numerals allotted, and description thereof will not be repeated.

It should be noted that, although a superconducting magnet for MRI (Magnetic Resonance Imaging) will be described in the following embodiment, the superconducting magnet is not limited to this usage and may be used for other usage. Moreover, although a superconducting magnet of a cylindrical type will be described, it is not limited to the superconducting magnet of the cylindrical type, and the present invention can be applied also to a superconducting magnet of an open type.

First Embodiment

FIG. 1 is a perspective view representing an appearance of an MRI apparatus. As shown in FIG. 1, an MRI apparatus 1 includes a static magnetic field generating unit 10 and a bed 30. Static magnetic field generating unit 10 includes a superconducting magnet, which will be described later, and generates a static magnetic field inside of a bore 20.

Figure 2:
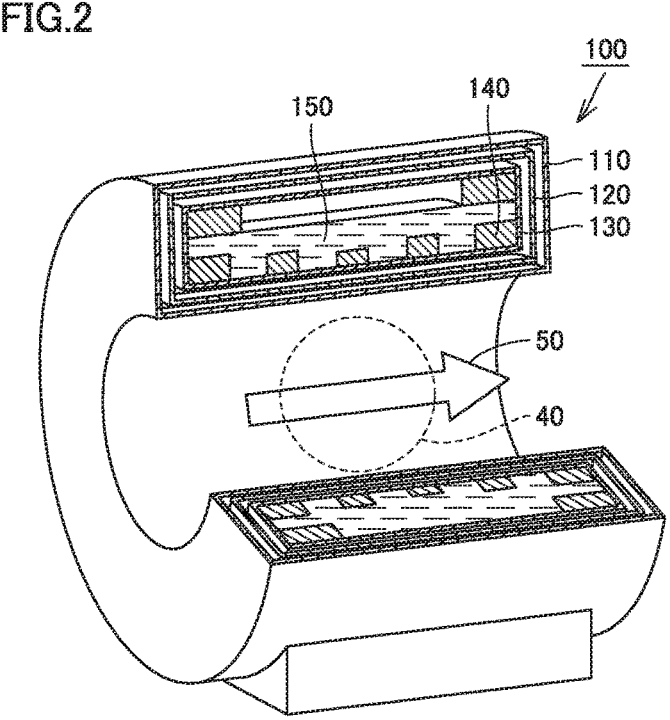
FIG. 2 is a cross-sectional view representing a structure of a superconducting magnet in accordance with a first embodiment of the present invention.

FIG. 2 is a cross-sectional view representing a structure of the superconducting magnet in accordance with the first embodiment of the present invention. As shown in FIG. 2, in a superconducting magnet 100 in accordance with the first embodiment of the present invention, a vacuum container 110 having a hollow cylindrical shape is arranged on an outermost side. Vacuum container 110 is constituted of nonmagnetic material such as stainless steel or aluminum to provide vacuum insulation between inside and outside of vacuum container 110.

A space in a cylinder center portion of vacuum container 110 is a bore portion corresponding to bore 20. The interior of vacuum container 110 is decompressed by a decompression device, which is not illustrated in the drawings, to provide vacuum. Vacuum container 110 is supported by a leg portion arranged on a lower portion such that a center axis of the bore portion is oriented in a horizontal direction.

In vacuum container 110, a radiation shield 120 is arranged, which has a hollow cylindrical shape substantially similar to vacuum container 110. Radiation shield 120 is constituted of, for example, nonmagnetic material such as aluminum exhibiting a high light reflectance. On a surface of radiation shield 120, multilayer heat insulating material (superinsulation), which is not illustrated in the drawings, is attached.

In radiation shield 120, a refrigerant container 130 is arranged, which has a hollow cylindrical shape substantially similar to radiation shield 120. Radiation shield 120 surrounds refrigerant container 130 and serves to provide heat insulation between refrigerant container 130 and vacuum container 110. Refrigerant container 130 is constituted of nonmagnetic material such as stainless steel or aluminum.

In refrigerant container 130, a superconducting coil 140 is accommodated. Superconducting coil 140 is wound at a bottom portion of refrigerant container 130 serving also as a winding frame. Refrigerant container 130 is filled with liquid helium 150 as a liquid refrigerant. Superconducting coil 140 is immersed in liquid helium 150 and cooled. Superconducting coil 140 is constituted of, for example, a wound superconducting wire which is formed by embedding niobium titanium alloy in a center portion of a matrix made of copper.

In such a manner, vacuum container 110 accommodates superconducting coil 140, refrigerant container 130, and radiation shield 120. When superconducting magnet 100 operates, a static magnetic field 50 in the arrow direction is generated in a static magnetic field region 40 in the area of the bore portion indicated by the dotted line in the drawing.

Figure 3:
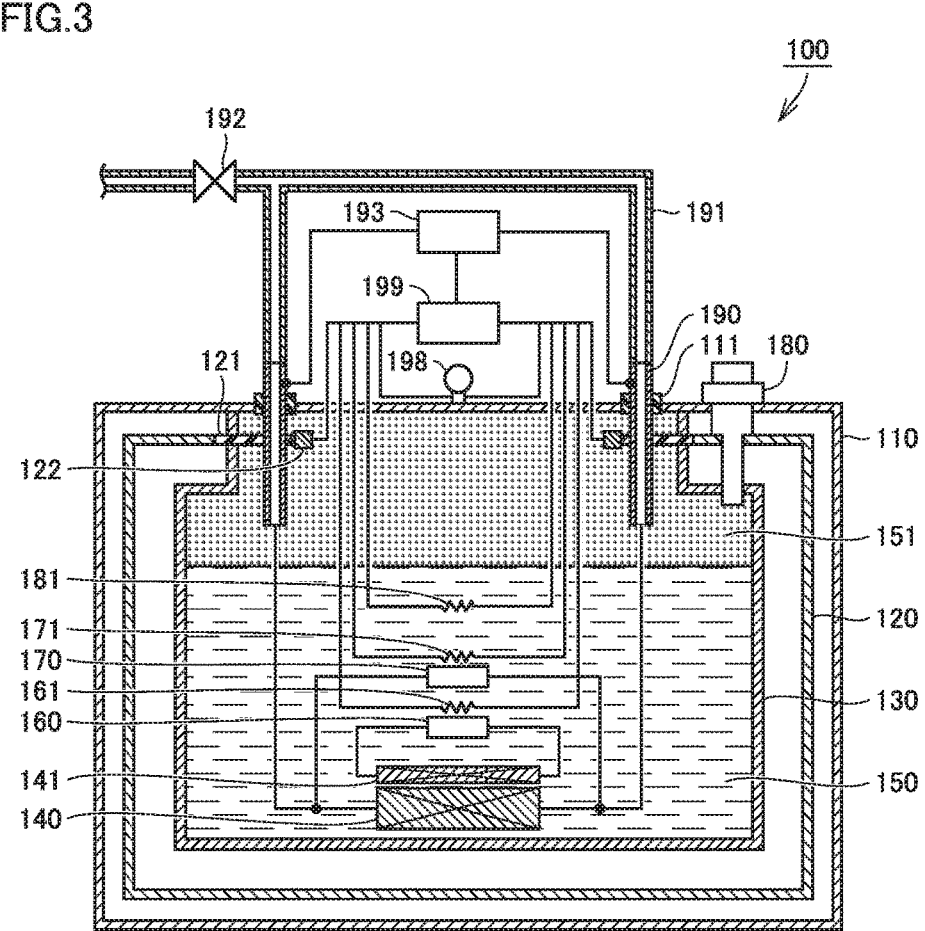
FIG. 3 is a cross-sectional view representing a configuration of the superconducting magnet in accordance with the same embodiment.

FIG. 3 is a cross-sectional view representing a configuration of the superconducting magnet in accordance with the present embodiment. In FIG. 3, each configuration is illustrated in a simplified manner for simplification.

As shown in FIG. 3, a disturbance magnetic field compensating coil 141 for suppressing influence of a disturbance magnetic field with respect to superconducting coil 140 is arranged outside of superconducting coil 140. Disturbance magnetic field compensating coil 141 is constituted of, for example, a wound superconducting wire which is formed by embedding niobium titanium alloy in a center portion of a matrix made of copper.

Moreover, a first persistent current switch 170 is connected to superconducting coil 140 electrically in serial. First persistent current switch 170 is constituted of, for example, a winding wire of a superconducting filament made of niobium titanium alloy and wound around a winding frame made of epoxy resin. A first resistive heating heater 171 having a heater wire wound therearound is arranged outside of first persistent current switch 170.

A second persistent current switch 160 is connected to disturbance magnetic field compensating coil 141 electrically in serial. Second persistent current switch 160 is constituted of, for example, a winding wire of a superconducting filament made of niobium titanium alloy and wound around a winding frame made of epoxy resin. Second resistive heating heater 161 having a heater wire wound therearound is arranged outside of second persistent current switch 160.

Superconducting magnet 100 in accordance with the present embodiment further includes a third resistive heating heater 181 which is arranged in refrigerant container 130 and gasifies liquid helium 150. It should be noted that, when electrical conduction to second resistive heating heater 161 can gasify a quantity of liquid helium 150 required to cool current lead 190 at the time of magnetizing and demagnetizing superconducting magnet 100 as described below, it is not necessary to provide third resistive heating heater 181.

Each of disturbance magnetic field compensating coil 141, first persistent current switch 170, first resistive heating heater 171, second persistent current switch 160, second resistive heating heater 161, and third resistive heating heater 181 is immersed in liquid helium 150 in refrigerant container 130.

Superconducting magnet 100 includes a refrigerating machine 180 for cooling an interior of refrigerant container 130 and radiation shield 120. As refrigerating machine 180, a Gifford-MacMahon type refrigerating machine or a pulse tube refrigerating machine having two refrigerating stages can be used.

A first refrigerating stage of refrigerating machine 180 is thermally in contact with radiation shield 120. A second refrigerating stage of refrigerating machine 180 is located at an upper portion in refrigerant container 130 and re-liquefies gasified helium gas 151.

Superconducting magnet 100 includes two tubular current leads 190 passing from outside of vacuum container 110 to inside of refrigerant container 130 to constitute flow paths of helium gas 151 and electrically connected to superconducting coil 140. Each current lead 190 has a straight-pipe outer shape, and only an upper end portion of current lead 190 is located outside of vacuum container 110.

In the present embodiment, material of current lead 190 contains phosphorous deoxidized copper as a main component. However, the main component of the material of current lead 190 is not limited to phosphorous deoxidized copper, and it may be brass or electrolytic copper.

A lower end portion of each current lead 190 is cooled to about 4K which is substantially the same as superconducting coil 140. Each current lead 190 is fixed in a state of being inserted to an annular fixation member 111, which is provided in vacuum container 110 and has an electrical insulation property. The exterior of vacuum container 110 is at a temperature of about 300K which is a room temperature.

A mid-temperature stage 121, for example, made of copper and having a block-like shape is connected to each current lead 190 at a position of about one-third of an overall length of current lead 190 on a lower end side of current lead 190 from a portion in contact with fixation member 111.

Each mid-temperature stage 121 is thermally in contact with radiation shield 120 while clamping a thermal anchor therebetween. Each mid-temperature stage 121 and radiation shield 120 are electrically insulated. A thermometer 122 arranged in vacuum container 110 for measuring the temperature of current lead 190 is connected to each mid-temperature stage 121. A platinum resistance thermometer exhibiting a favorable measurement accuracy in a cryogenic temperature region is used as thermometer 122. However, not limited to this, a thermoelectric couple may be used.

An external pipe 191, which is in communication with current lead 190 and has an electrical insulation property, is connected to an upper end portion of each current lead 190. In the present embodiment, two current leads 190 and one branched external pipe 191 are connected. An open valve for opening and closing external pipe 191 is provided at an unbranched portion of external pipe 191. For example, a check valve or an electromagnetic valve can be used as open valve 192.

Superconducting magnet 100 includes a manometer 198 for measuring the pressure inside of refrigerant container 130. Manometer 198 measures the pressure of helium gas 151 in refrigerant container 130.

Moreover, superconducting magnet 100 includes a power source 193 arranged outside of vacuum container 110 and electrically connected to each current lead 190.

Further, superconducting magnet 100 includes a control unit 199 connected to each of power source 193, manometer 198, and two thermometers 122. Control unit 199 is arranged outside of vacuum container 110. A measurement value of each thermometer 122 and a measurement value of manometer 198 are inputted to control unit 199.

Control unit 199 is electrically connected to each of first resistive heating heater 171, second resistive heating heater 161, and third resistive heating heater 181. Therefore, each of first resistive heating heater 171, second resistive heating heater 161, and third resistive heating heater 181 is connected to power source 193 through control unit 199.

It should be noted that superconducting magnet 100 may have a function to measure the liquid amount of liquid helium 150 in refrigerant container 130, a function to measure the temperature of radiation shield 120, a function to measure the temperature of the second refrigerating stage of refrigerating machine 180, a function to shut off the magnetic field generated by superconducting coil in emergency, a function to control a compressor of refrigerating machine 180, or the like.

In the following, an operation of magnetizing superconducting coil 140 in superconducting magnet 100 in accordance with the present embodiment will be described. To use superconducting magnet 100, it is necessary to cool superconducting coil 140 to a cryogenic temperature state. Firstly, after producing a vacuum in vacuum container 110, the interior of refrigerant container 130 is filled with nitrogen gas. After that, refrigerating machine 180 is inserted into vacuum container 110 and then operated.

The first refrigerating stage of refrigerating machine 180 cools radiation shield 120 to about 50K. Superconducting coil 140 is cooled by liquid nitrogen to about 77K. After that, helium gas fills refrigerant container 130 to replace nitrogen. Finally, superconducting coil 140 is cooled by liquid helium 150 to about 4K.

Next, control unit 199 allows a current from power source 193 to flow into each of first resistive heating heater 171 and second resistive heating heater 161. Accordingly, a resistance is generated in a superconducting filament of each of first persistent current switch 170 and second persistent current switch 160.

Generating the resistance in the superconducting filament of second persistent current switch 160 reduces a current induced by disturbance magnetic field compensating coil 141 due to an influence of the magnetic field received from the disturbance magnetic field, so that an output of disturbance magnetic field compensating coil 141 is reset.

After that, control unit 199 allows a current from power source 193 to flow into third resistive heating heater 181. Accordingly, liquid helium 150 is evaporated by Joule's heat of third resistive heating heater 181, so that the pressure in refrigerant container 130 is raised. At this time, open valve 192 is in an open state.

In the present embodiment, conditions for starting magnetization are set and inputted to control unit 199. The conditions are defined that a measurement value of manometer 198 is higher than or equal to a gauge pressure of 7000 Pa and a measurement value of each thermometer 122 is lower than or equal to 80K.

In other words, control unit 199 raises an output of power source 193 to vary a value of a current flowing into superconducting coil 140 only when a measurement value of manometer 198 is higher than or equal to a set value and a measurement value of thermometer 122 is lower than or equal to a set value.

Therefore, when the pressure value of helium gas 151 in refrigerant container 130 is lower than 7000 Pa, or when the temperature in mid-temperature stage 121 is higher than 80K, control unit 199 determines that magnetization cannot be performed, and it does not raise an output of power source 193.

When the conditions for starting magnetization are satisfied, and control unit 199 raises an output of power source 193, almost no current flows into first persistent current switch 170 in which the resistance is generated, and a current mainly flows into superconducting coil 140 through current lead 190.

At this time, although Joule's heat is generated in current lead 190, the rise in temperature of current lead 190 is suppressed since current lead 190 is cooled by helium gas 151 flowing in current lead 190. In other words, helium gas 151 gasified in refrigerant container 130 flows out to external pipe 191 and is exhausted while cooling current lead 190.

Even if current lead 190 is frozen, and helium gas 151 cannot flow in current lead 190, the rise in temperature of current lead 190 can be suppressed since helium gas 151 can flow in current lead 190 when the ice is melted by Joule's heat generated in current lead 190.

When the ice cannot be melted by Joule's heat, current lead 190 is not sufficiently cooled by helium gas 151, so that the temperature of current lead 190 rises. In this case, control unit 199 recognizing that the temperature of mid-temperature stage 121 became higher than 80K based on the inputted measurement value of thermometer 122 stops the rise in an output of power source 193. Accordingly, burn-out of current lead 190 due to overheating is prevented.

After an output of power source 193 reaches a set output in a state where the rise in temperature of current lead 190 is suppressed, control unit 199 stops electric conduction to first resistive heating heater 171. Accordingly, first persistent current switch 170 is cooled by liquid helium 150 to be in a superconducting state.

After first persistent current switch 170 is shifted to the superconducting state, control unit 199 lowers an output of power source 193. At this time, the amount of current flowing in superconducting coil 140 is not varied, and the amount of current flowing in first persistent current switch 170 increases. When the output of power source 193 becomes zero, the same amount of current flows into superconducting coil 140 and first persistent current switch 170. In this state, even when the electrical connection with power source 193 is disconnected, a current flows continuously in a closed loop constituted of superconducting coil 140 and first persistent current switch 170. Accordingly, the magnetization of superconducting magnet 100 is completed.

Next, an operation of demagnetizing superconducting coil 140 in superconducting magnet 100 in accordance with the present embodiment will be described.

Firstly, control unit 199 allows a current from power source 193 to flow into second resistive heating heater 161. Accordingly, a resistance is generated in a superconducting filament of second persistent current switch 160. Generating the resistance in the superconducting filament of second persistent current switch 160 reduces a current induced by disturbance magnetic field compensating coil 141 due to an influence of the magnetic field from disturbance magnetic field, so that the output of disturbance magnetic field compensating coil 141 is reset.

Next, control unit 199 allows a current from power source 193 to flow into third resistive heating heater 181. Accordingly, liquid helium 150 is evaporated by Joule's heat of third resistive heating heater 181, so that the pressure in refrigerant container 130 is raised. At this time, open valve 192 is in an open state.

In the present embodiment, the conditions for starting demagnetization are set and inputted to control unit 199. The conditions are defined that a measurement value of manometer 198 is higher than or equal to a gauge pressure of 7000 Pa and a measurement value of each thermometer 122 is lower than or equal to 80K.

In other words, control unit 199 may raise the output of power source 193 to vary a value of a current flowing into superconducting coil 140 only when the measurement value of manometer 198 is higher than or equal to a set value and a measurement value of thermometer 122 is lower than or equal to a set value.

Therefore, when the pressure value of helium gas 151 in refrigerant container 130 is lower than 7000 Pa, or when the temperature of mid-temperature stage 121 is higher than 80K, control unit 199 determines that demagnetization cannot be performed, and it does not raise the output of power source 193.

When the conditions for starting demagnetization are satisfied, and control unit 199 raises the output of power source 193, since the direction of a current flowing from power source 193 and the direction of a current flowing in the closed loop are opposite to each other, the amount of current flowing in superconducting coil 140 does not vary, and the amount of current flowing in first persistent current switch 170 is reduced.

At this time, although the Joule's heat is generated in current lead 190, the rise in temperature of current lead 190 is suppressed since current lead 190 is cooled by helium gas 151 flowing in current lead 190. In other words, helium gas 151 gasified in refrigerant container 130 flows out to external pipe 191 and is exhausted while cooling current lead 190.

Even if the temperature of current lead 190 is raised, control unit 199 recognizing that the temperature of mid-temperature stage 121 became higher than 80K based on the inputted measurement value of thermometer 122 stops the rise in the output of power source 193. Accordingly, burn-out due to overheating of current lead 190 is prevented.

In the state where the rise in temperature of current lead 190 is suppressed, after the output current value of power source 193 becomes equal to the value of current flowing in superconducting coil 140, control unit 199 conducts electricity to first resistive heating heater 171. Accordingly, a resistance is generated in the superconducting filament of first persistent current switch 170, so that first persistent current switch 170 is shifted to a normal conducting state. At this time, the value of a current flowing in first persistent current switch 170 is zero.

In this state, lowering the output of power source 193 reduces a value of current flowing in superconducting coil 140. When the value of current flowing in superconducting coil 140 becomes zero, the demagnetization of superconducting magnet 100 is completed.

As described above, in superconducting magnet 100 in accordance with the present embodiment, the magnetization and demagnetization of superconducting magnet 100 are not performed unless control unit 199 confirms that enough quantity of helium gas 151 is present in refrigerant container 130 and that current lead 190 is not overheated. Accordingly, burn-out of current lead 190 due to overheating can be prevented.

It should be noted that, in the present embodiment, a main component of the material of current lead 190 is phosphorous deoxidized copper. The reason will be described as follows.

In superconducting magnet 100 in accordance with the present embodiment, current lead 190 of a fixed type is used. Therefore, intrusion of heat from outside into refrigerant container 130 through current lead 190 is always present. Therefore, material of current lead 190 is preferably material exhibiting a low thermal conductivity. Moreover, at the time of magnetization and demagnetization of superconducting magnet 100, intrusion of heat by Joule's heat generated in current lead 190 is present. To reduce the heat intrusion by the Joule's heat, material of current lead 190 is preferably material exhibiting a low electrical resistivity.

Therefore, material of current lead 190 is preferably material exhibiting both low thermal conductivity and low electrical resistivity. Accordingly, for each of phosphorous deoxidized copper, brass, electrolytic copper, and SUS304 as alternatives of material of current lead 190, a temperature dependency in a value of a product of a thermal conductivity and an electrical resistivity was examined.

Figure 4:
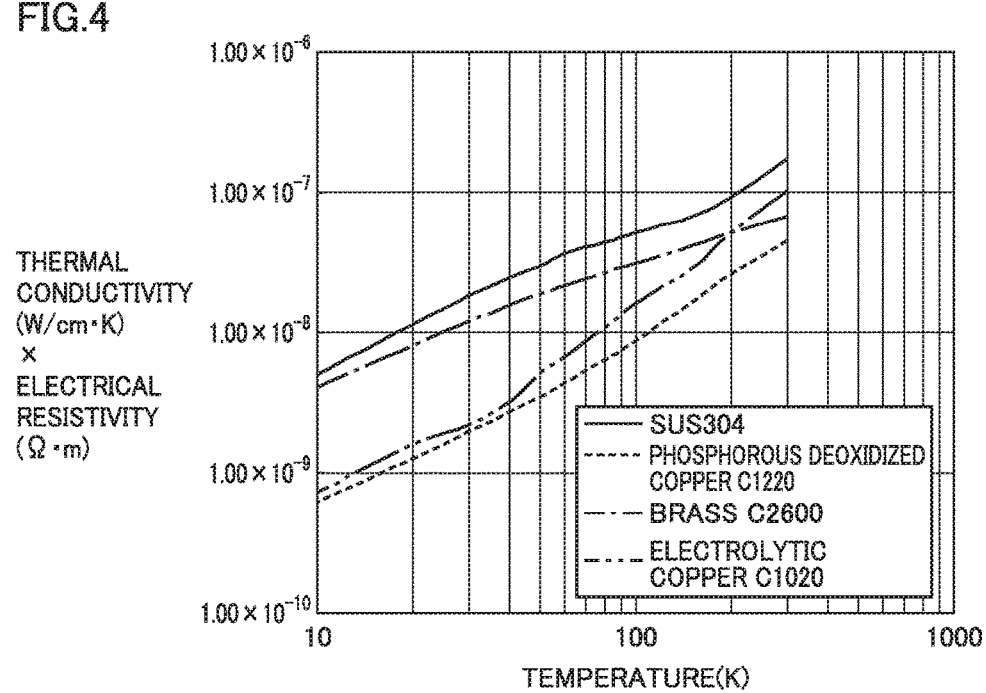
FIG. 4 represents a temperature dependency in a value of a product of a thermal conductivity and an electrical resistivity for each of phosphorous deoxidized copper, brass, electrolytic copper, and SUS304.

FIG. 4 is a graph representing a temperature dependency in a value of a product of a thermal conductivity and an electrical resistivity for each of phosphorous deoxidized copper, brass, electrolytic copper, and SUS304. In FIG. 4, the vertical axis denotes a value of a product between a thermal conductivity and an electrical resistivity, and the horizontal axis denotes the temperature.

As shown in FIG. 4, as compared to brass, electrolytic copper, and SUS304, phosphorous deoxidized copper has a smaller value of a product of a thermal conductivity and an electrical resistivity in all temperature zones. Therefore, setting phosphorous deoxidized copper as a main component of material of current lead 190 can reduce the intrusion of heat into refrigerant container 130 and suppress generation of burn-out of current lead 190 due to the Joule's heat.

In the following, a superconducting magnet in accordance with a second embodiment of the present invention will be described. Since a superconducting magnet 100a in accordance with the present embodiment differs from superconducting magnet 100 in accordance with the first embodiment in that a flow meter is used in place of the manometer, description as to other configurations will not be repeated.

Second Embodiment

Figure 5:
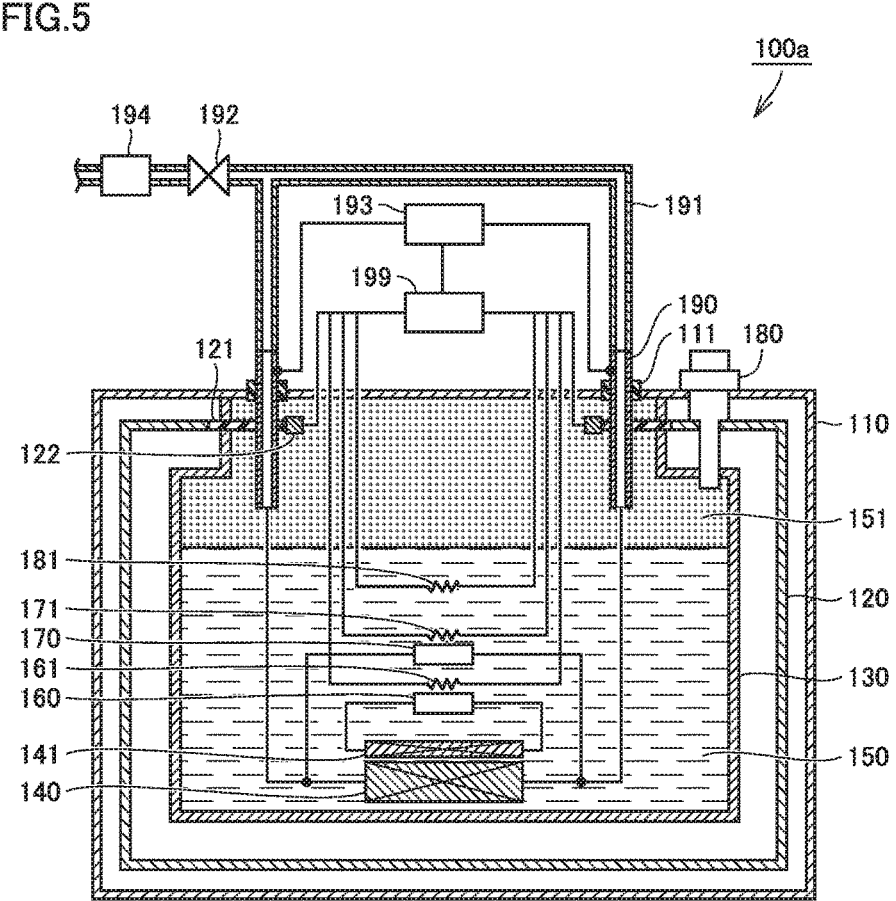
FIG. 5 is a cross-sectional view representing a configuration of a superconducting magnet in accordance with a second embodiment of the present invention.

FIG. 5 is a cross-sectional view representing a configuration of a superconducting magnet in accordance with the second embodiment of the present invention. In FIG. 5, a cross section viewed from the same direction as FIG. 3 is shown.

As shown in FIG. 5, superconducting magnet 100a in accordance with the second embodiment of the present invention includes a flow meter 194 measuring a flow rate of helium gas 151 passing through an interior of current lead 190. Specifically, flow meter 194 is attached to an unbranched portion of external pipe 191. Therefore, flow meter 194 measures a total flow rate of helium gas 151 passing through the interior of two current leads 190. The measurement value of flow meter 194 is inputted to control unit 199.

In the present embodiment, the conditions for starting magnetization and for starting demagnetization are set and inputted to control unit 199. The conditions are defined that the measurement value of flow meter 194 is higher than or equal to 25 L/min, and the measurement value of each thermometer 122 is lower than or equal to 80K.

In other words, control unit 199 raises the output of power source 193 to vary the value of a current flowing into superconducting coil 140 only when the measurement value of flow meter 194 is higher than or equal to a set value and the measurement value of thermometer 122 is lower than or equal to a set value.

Therefore, when the flow rate value of helium gas 151 in external pipe 191 is lower than 25 L/min, or when the temperature of mid-temperature stage 121 is higher than 80K, control unit 199 determines that magnetization and demagnetization cannot be performed, and it does not raise the output of power source 193.

If current lead 190 is frozen and helium gas 151 cannot flow in current lead 190, control unit 199 recognizing that the amount of helium gas 151 flowing in current lead 190 is small based on the inputted measurement value of flow meter 194 stops the raise in output of power source 193. Accordingly, burn-out of current lead 190 due to overheating is prevented.

As described above, in superconducting magnet 100a in accordance with the present embodiment, magnetization and demagnetization of superconducting magnet 100a are not performed unless control unit 199 confirms that enough amount of helium gas 151 flows in current lead 190 and that current lead 190 is not overheated. Therefore, burn-out of current lead 190 due to overheating is prevented.

In the following, a superconducting magnet in accordance with a third embodiment of the present invention will be described. Since a superconducting magnet 100b in accordance with the present embodiment is different from superconducting magnet 100 in accordance with the first embodiment only in that a refrigerating machine operation switcher is used in place of the third resistive heating heater, description as to other configurations will not be repeated.

Third Embodiment

Figure 6:
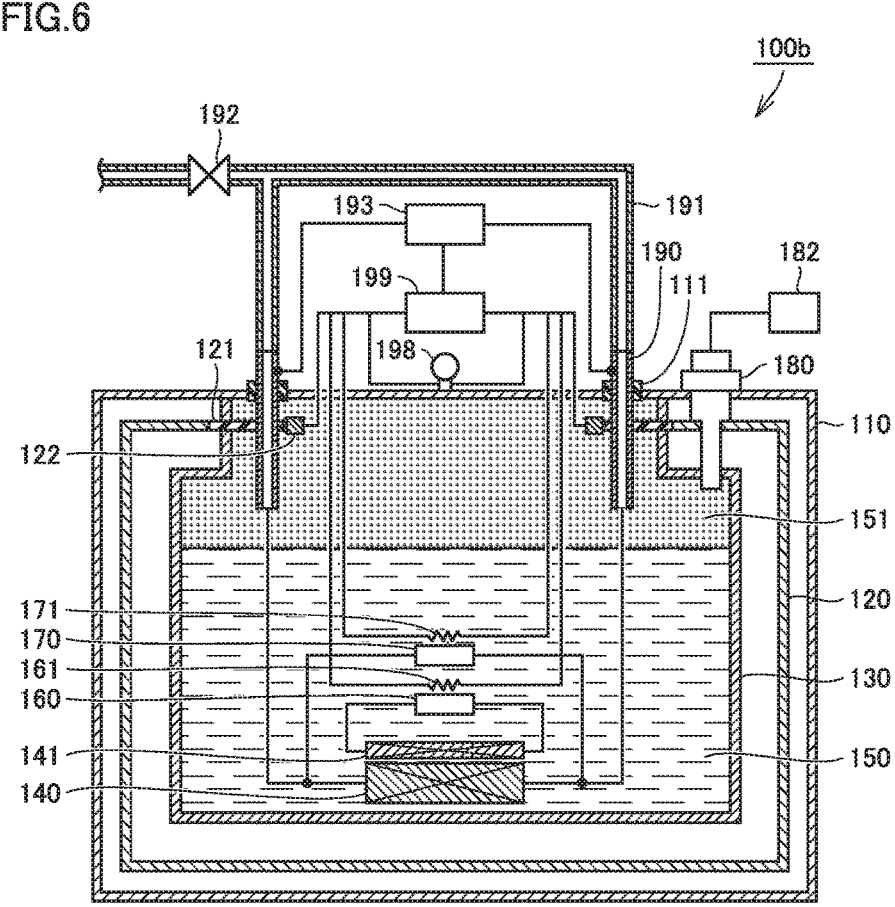
FIG. 6 is a cross-sectional view representing a configuration of a superconducting magnet in accordance with a third embodiment of the present invention.

FIG. 6 is a cross-sectional view representing a configuration of a superconducting magnet in accordance with the third embodiment of the present invention. In FIG. 6, a cross section viewed from the same direction as FIG. 3 is shown.

As shown in FIG. 6, superconducting magnet 100b in accordance with the third embodiment of the present invention includes a refrigerating machine operation switcher 182 stopping a refrigerating machine 180 to raise the temperature in refrigerant container 130 to gasify liquid helium 150. Refrigerating machine operation switcher 182 is connected to refrigerating machine 180. Moreover, refrigerating machine operation switcher 182 is electrically connected to control unit 199.

In superconducting magnet 100b in accordance with the present embodiment, control unit 199 stops refrigerating machine 180 by means of refrigerating machine operation switcher 182 before magnetizing and demagnetizing superconducting magnet 100b. In the state where refrigerating machine 180 is stopped, liquid helium 150 is evaporated by intrusion of heat into refrigerant container 130. Consequently, the pressure value of helium gas 151 in refrigerant container 130 is raised to be higher than or equal to 7000 Pa.

Also in such a case, liquid helium 150 can be gasified by a quantity required for cooling current lead 190 at the time of magnetizing and demagnetizing superconducting magnet 100b.

It should be noted that superconducting magnet 100b may include both the third resistive heating heater and refrigerating machine operation switcher 182. In this case, conducting electricity to the third resistive heating heater in the state where refrigerating machine 180 is stopped by refrigerating machine operation switcher 182 can gasify liquid helium 150 in a short period of time by an amount required to cool current lead 190 at the time of magnetizing and at the time of demagnetizing.

In the following, a superconducting magnet in accordance with a fourth embodiment of the present invention will be described. Since a superconducting magnet 100c in accordance with the present embodiment is different from superconducting magnet 100 in accordance with the first embodiment only in that a fourth resistive heating heater and a power source for the fourth resistive heating heater is further included, description as to other configurations will not be repeated.

Fourth Embodiment

Figure 7:
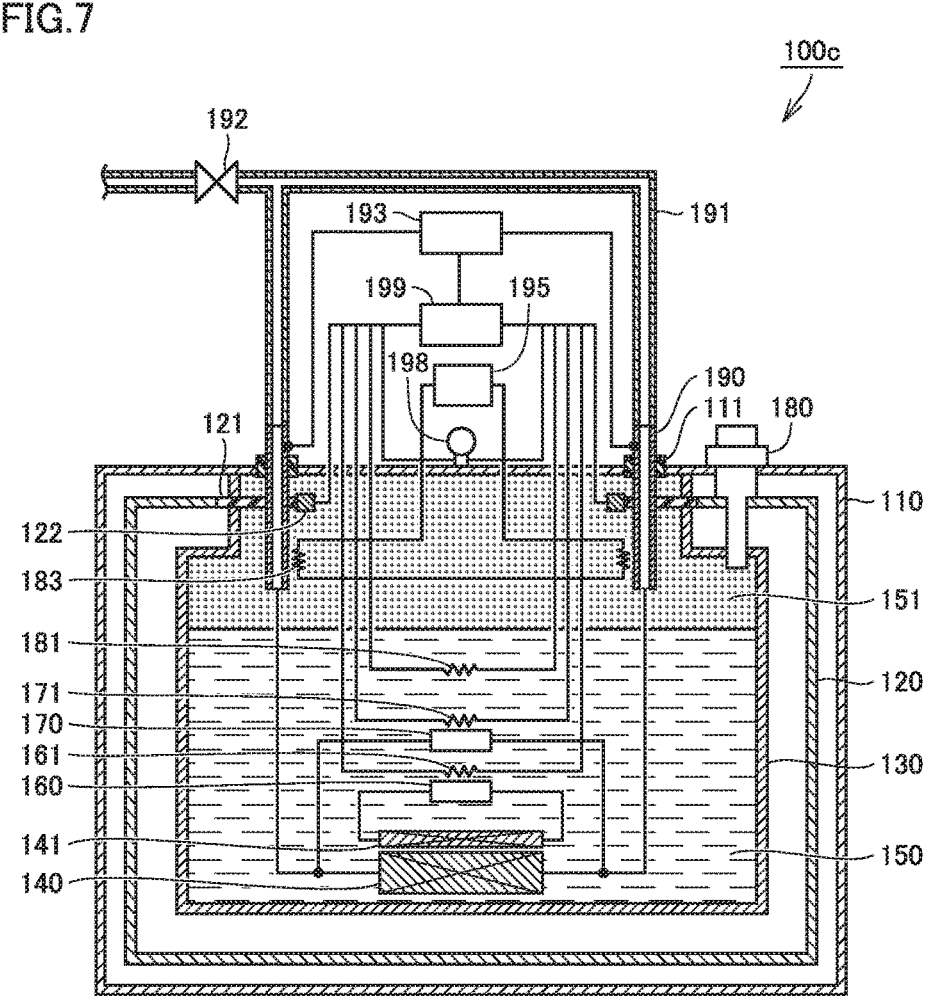
FIG. 7 is a cross-sectional view representing a configuration of a superconducting magnet in accordance with a fourth embodiment of the present invention.

FIG. 7 is a cross-sectional view representing a configuration of the superconducting magnet in accordance with the fourth embodiment of the present invention. In FIG. 7, a cross section viewed from the same direction as FIG. 3 is shown.

As shown in FIG. 7, superconducting magnet 100c in accordance with the fourth embodiment of the present invention includes two resistive heating heaters 183 arranged adjacent to current lead 190 in refrigerant container 130 for heating current lead 190.

Each fourth resistive heating heater 183 is constituted of a wound heater wire. Fourth resistive heating heater 183 is thermally in contact at a position of about one-fourth of an overall length of current lead 190 on an upper end side of current lead 190 from a lower end portion of current lead 190. One fourth resistive heating heater 183 is thermally in contact with one current lead 190 to correspond in a one-by-one relationship. Current lead 190 and fourth resistive heating heater 183 are electrically insulated.

Fourth resistive heating heater 183 is electrically connected with a power source 195 arranged outside of vacuum container 110. Power source 195 is electrically connected with control unit 199.

In superconducting magnet 100c in accordance with the present embodiment, when current lead 190 is frozen and helium gas 151 cannot flow in current lead 190, control unit 199 activates power source 195 to conduct electricity to fourth resistive heating heater 183.

When the measurement value of manometer 198 is higher than or equal to 7000 Pa and the measurement value of thermometer 122 becomes higher than 80K, control unit 199 determines that it is in a state where current lead 190 is frozen and helium gas 151 cannot flow in current lead 190.

Since helium gas 151 can flow in current lead 190 by heating current lead 190 by means of fourth resistive heating heater 183 to melt the ice, the rise in temperature of current lead 190 can be suppressed.

Control unit 199 stops conducting electricity to fourth resistive heating heater 183 by means of power source 195 after confirming that the measurement value of thermometer 122 becomes lower than or equal to 80K. As described above, by assuring that helium gas 151 cools current lead 190, burn-out of current lead 190 due to overheating is prevented.

Fourth resistive heating heater 183 and power source 195 may be provided in superconducting magnets 100a, 100b in accordance with the second and third embodiments.

It should be understood that the embodiments disclosed herein are only by way of examples, and not to be taken by way of limitation. Therefore, the technical scope of the present invention is not limited by the description above, but rather by the terms of the appended claims. Further, any modifications within the scope and meaning equivalent to the terms of the claims are included.

REFERENCE SIGNS LIST

1 MRI apparatus; 10 static magnetic field generating unit; 20 bore; 30 bed; 40 static magnetic field region; 50 static magnetic field; 100, 100a, 100b, 100c superconducting magnet; 110 vacuum container; 111 fixation member; 120 radiation shield; 121 mid-temperature stage; 122 thermometer; 130 refrigerant container; 140 superconducting coil; 141 disturbance magnetic field compensating coil; 150 liquid helium; 151 helium gas; 160 second persistent current switch; 161 second resistive heating heater; 170 first persistent current switch; 171 first resistive heating heater; 180 refrigerating machine; 181 third resistive heating heater; 182 refrigerating machine operation switcher; 183 fourth resistive heating heater; 190 current lead; 191 external pipe; 192 open valve; 193, 195 power source; 194 flow meter; 198 manometer; 199 control unit.

The invention claimed is:

1. A superconducting magnet, comprising:
a superconducting coil;
a refrigerant container accommodating said superconducting coil which is in a state of being immersed in a liquid refrigerant;
a radiation shield surrounding said refrigerant container;
a vacuum container accommodating said superconducting coil, said refrigerant container, and said radiation shield;
a refrigerating machine cooling an interior of said refrigerant container and said radiation shield;
a tubular current lead passing from outside of said vacuum container to inside of said refrigerant container to constitute a flow path of said gasified refrigerant and being electrically connected to said superconducting coil;
a power source arranged outside of said vacuum container and electrically connected to said current lead;
a manometer measuring a pressure inside of said refrigerant container;
a thermometer arranged in said vacuum container to measure a temperature of said current lead; and
a control unit connected to each of said power source, said manometer, and said thermometer;
a disturbance magnetic field compensating coil arranged outside of said superconducting coil and immersed in said refrigerant in said refrigerant container for suppressing an influence of a disturbance magnetic field with respect to said superconducting coil;
a persistent current switch immersed in said refrigerant in said refrigerant container and connected to said disturbance magnetic field compensating coil electrically in serial; and
a heater arranged adjacent to said persistent current switch in said refrigerant container, immersed in said refrigerant, and electrically connected to said control unit,
said control unit allowing a current from said power source to flow into said heater to gasify said refrigerant of an amount required cool said current lead while resetting an output of said disturbance magnetic field compensating coil by means of said persistent current switch,
said control unit raising an output of said power source to vary a value of a current flowing into said superconducting coil only when a measurement value of said manometer is higher than or equal to a set value and a measurement value of said thermometer is lower than or equal to a set value.

2. The superconducting magnet according to claim 1, further comprising a heater arranged adjacent to said current lead in said refrigerant container to heat said current lead.

3. The superconducting magnet according to claim 1, wherein material of said current lead contains phosphorous deoxidized copper as a main component.

4. A superconducting magnet, comprising:
a superconducting coil;
a refrigerant container accommodating said superconducting coil which is in a state of being immersed in a liquid refrigerant;
a radiation shield surrounding said refrigerant container;
a vacuum container accommodating said superconducting coil, said refrigerant container, and said radiation shield;
a refrigerating machine cooling an interior of said refrigerant container and said radiation shield;
a tubular current lead passing from outside of said vacuum container to inside of said refrigerant container to constitute a flow path of said gasified refrigerant and being electrically connected to said superconducting coil;
a power source arranged outside of said vacuum container and electrically connected to said current lead;
a flow meter measuring a flow rate of said gasified refrigerant through inside of said current lead;
a thermometer arranged in said vacuum container to measure a temperature of said current lead; and
a control unit connected to each of said power source, said flow meter, and said thermometer;
a disturbance magnetic field compensating coil arranged outside of said superconducting coil and immersed in said refrigerant in said refrigerant container for suppressing an influence of a disturbance magnetic field with respect to said superconducting coil;
a persistent current switch immersed in said refrigerant in said refrigerant container and connected to said disturbance magnetic field compensating coil electrically in serial; and
a heater arranged adjacent to said persistent current switch in said refrigerant container, immersed in said refrigerant, and electrically connected to said control unit, said control unit allowing a current from said power source to flow into said heater to gasify said refrigerant of an amount required cool said current lead while resetting an output of said disturbance magnetic field compensating coil by means of said persistent current switch, said control unit raising an output of said power source to vary a value of a current flowing into said superconducting coil only when a measurement value of said flow meter is higher than or equal to a set value and a measurement value of said thermometer is lower than or equal to a set value.

\* \* \* \* \*